US009504525B2

(12) United States Patent
Park (10) Patent No.: US 9,504,525 B2
(45) Date of Patent: Nov. 29, 2016

(54) HANDPIECE LASER TREATMENT APPARATUS CAPABLE OF ADJUSTING LENGTH OF OPTICAL FIBER

(71) Applicant: In Bae Park, Boryeong-si (KR)

(72) Inventor: In Bae Park, Boryeong-si (KR)

(*) Notice: Subject to any disclaimer, the term of this patent is extended or adjusted under 35 U.S.C. 154(b) by 0 days.

(21) Appl. No.: 14/941,657

(22) Filed: Nov. 15, 2015

(65) Prior Publication Data

US 2016/0184018 A1  Jun. 30, 2016

(30) Foreign Application Priority Data

Nov. 18, 2014  (KR) .................. 10-2014-0160910

(51) Int. Cl.
*A61B 18/22* (2006.01)
*A61B 18/00* (2006.01)
*A61B 18/20* (2006.01)

(52) U.S. Cl.
CPC ...... *A61B 18/22* (2013.01); *A61B 2018/00196* (2013.01); *A61B 2018/202* (2013.01); *A61B 2018/225* (2013.01); *A61B 2018/2244* (2013.01)

(58) Field of Classification Search
CPC .............. A61B 18/22; A61B 2018/00196; A61B 2018/225
USPC ....................... 606/15, 16; 607/89
See application file for complete search history.

(56) References Cited

U.S. PATENT DOCUMENTS

| | | | | |
|---|---|---|---|---|
| 4,048,743 A | * | 9/1977 | Lapinski ................ | A01K 91/02 43/17.5 |
| 5,156,604 A | * | 10/1992 | Hessel ................... | A61B 1/317 600/204 |
| 5,571,098 A | * | 11/1996 | Domankevitz ........ | A61B 18/22 606/15 |
| 5,688,264 A | * | 11/1997 | Ren ..................... | A61F 9/00821 606/13 |
| 2003/0114901 A1 | | 6/2003 | Loeb et al. | |
| 2004/0010248 A1 | * | 1/2004 | Appling ................ | A61B 18/24 606/15 |
| 2006/0173448 A1 | | 8/2006 | Scheller et al. | |
| 2007/0088218 A1 | | 4/2007 | Mcintyre et al. | |
| 2007/0157407 A1 | * | 7/2007 | Lin ........................ | A46B 3/08 15/184 |
| 2009/0094840 A1 | * | 4/2009 | Kanemoto ............. | B26B 5/001 30/162 |
| 2012/0283804 A1 | * | 11/2012 | Kang .................. | A61F 9/00802 607/89 |

FOREIGN PATENT DOCUMENTS

| | | |
|---|---|---|
| KR | 10-2007-0108132 | 11/2007 |
| KR | 10-2007-0108132 A | 11/2007 |
| KR | 10-1386137 | 4/2014 |
| KR | 10-1448860 | 10/2014 |

OTHER PUBLICATIONS

The internet webpage https://www.thorlabs.com/thorproduct.cfm?partnumber=S90R dated Dec. 12, 2012 and retreived on Jun. 20, 2016.*
English Translation of 10-1448860.
English Translation of 10-1386137.
English Translation of 10-2007-0108132.

* cited by examiner

*Primary Examiner* — Lynsey Crandall
*Assistant Examiner* — Nathan J Jenness
(74) *Attorney, Agent, or Firm* — KORUS Patent, LLC; Seong Il Jeong (57) ABSTRACT

The present invention relates generally to a handpiece laser treatment apparatus for treating an affected area by irradiating lasers thereto. More particularly, the present invention relates to a handpiece laser treatment apparatus capable of adjusting the drawn length of an optical fiber in which laser is irradiated. The handpiece laser treatment apparatus capable of adjusting the length of optical fiber according to the present invention comprises: a laser module for generating a laser; an optical fiber that is connected to the laser module so that the laser is irradiated to the outside; a main body in which the laser module is inserted and disposed in the inside and the optical fiber is projected forwardly; and a slider for adjusting the length of the optical fiber which is projected in front of the body.

4 Claims, 8 Drawing Sheets

Prior Art

HANDPIECE LASER TREATMENT APPARATUS CAPABLE OF ADJUSTING LENGTH OF OPTICAL FIBER

CROSS-REFERENCE TO RELATED APPLICATION

This application claims the benefit of Korean Patent Application No. 10-2014-0160910, filed on Nov. 18, 2014, which is hereby incorporated by reference herein in its entirety.

BACKGROUND

1. Technical Field

The present invention relates generally to a handpiece laser treatment apparatus for treating an affected area by irradiating lasers thereto. More particularly, the present invention relates to a handpiece laser treatment apparatus capable of adjusting the drawn length of an optical fiber in which laser is irradiated.

2. Description of the Related Art

In general, the laser treatment is effectively used in the treatment of skin diseases such as hair removal and vascular disorders. Moreover, treatments using lasers are utilized for ophthalmic, dentistry and surgery or dermatology. Laser treatment apparatus for laser surgery is disclosed in Korean Patent Registration No. 10-1386137.

Figure 1:
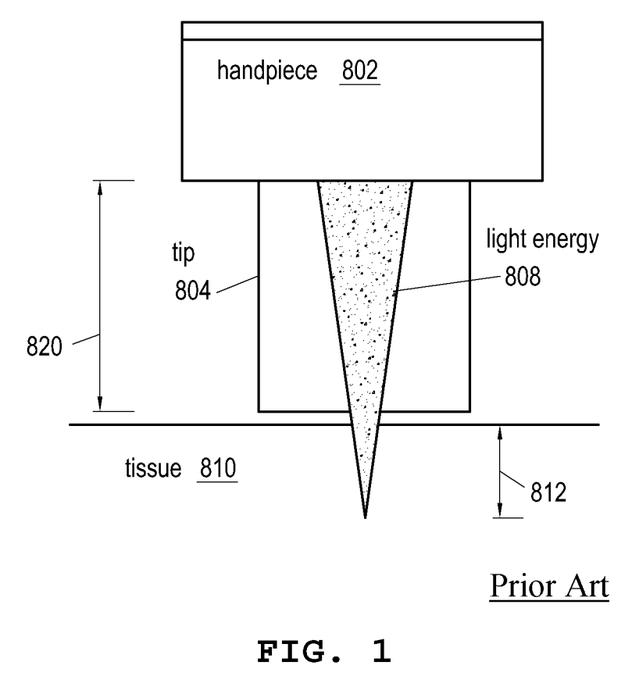
FIG. 1 is a side view showing the handpiece connected with a conventional treatment system.

On the other hand, a conventional medical laser treatment system is in contact with the tissue 810 of the parts to be treated and requires washing and special control to maintain the cleanliness and efficiency of the system. In response to these requirements, Korean Patent Publication No. 10-2007-0108132 discloses interchangeable tips coupled to the handpiece of the treatment system FIG. 1 is a side view of a handpiece coupled to a conventional treatment system. The medical laser treatment system including interchangeable tips comprises an electromagnetic energy source for transmitting the treatment energy 808; a handpiece 802 having the distal end and coupled to the electro magnetic energy source to transmit a treatment energy; and two or more interchangeable tips 804 which can be removably attached to the distal end of the handpiece 802. The tip 804 is attached to the handpiece 802 to transmit the treatment energy 808 from the distal end of the handpiece 802 to a target area for treatment. However, these tips have problems where replacement as well as washing and management for re-use are required and the replacement of the tip is troublesome.

SUMMARY

The present invention has been made keeping in mind the above problems encountered in the prior arts, and an object of the present invention is to provide a handpiece laser treatment apparatus capable of adjusting the length of an optical fiber for re-using it conveniently and hygenically by cutting a part of the optical fiber exposed to the outside upon treatment of the affected area and then drawing out the non-exposed optical fiber.

In order to accomplish the above objects, the handpiece laser treatment apparatus capable of adjusting the length of the optical fiber according to the present invention comprises: a laser module for generating a laser; an optical fiber that is connected to the laser module so that laser is irradiated to the outside; a main body in which the laser module is inserted and disposed in the inside and the optical fiber is projected forwardly; and a slider for adjusting the length of the optical fiber which is projected in front of the body.

Also, the slider adjusts the drawn length of the optical fiber by moving the laser module in a forward and backward direction of the main body.

In the main body, a guide groove is formed so that the laser module and the slider are connected; and the slider includes a moving part to move along the guide groove in a forward and backward direction of the main body, and a connecting part which is inserted into the guide groove and connects the laser module and the moving part.

Further, in the main body, a plurality of fixing grooves communicating with the guide groove are formed spaced apart from each other in a forward and backward direction of the main body; the width of the guide groove is smaller than the width of the fixing groove; and the width of the cross-section of the connecting part is larger than the width of the guide groove and less than or equal to the width of the fixing groove.

Further, the main body comprises a easing where the laser module is inserted and disposed in the inside and the optical fiber is projected forwardly; and a slide cover which is mounted on the casing and formed of the guide groove, wherein the slide cover is made of an elastic material and is elastically deformed upon movement of the slider, thus extending the width of the guide groove.

Further, the handpiece laser treatment apparatus capable of adjusting the length of optical fiber according to the present invention may further comprise a cutter for cutting the optical fiber.

Further, the cutter includes a coupling member which is detachably coupled to the rear side of the main body, and a cutting blade which is attached to the coupling body, wherein a blade groove in which the cutting blade is inserted is formed at the rear side of the main body.

In the handpiece laser treatment apparatus capable of adjusting the length of optical fiber according to the present invention, the length of the optical fiber to be projected in front of the main body can be adjusted by drawing out the length of the optical fiber using a slider, and the optical fiber can be conveniently and hygienically re-used by drawing out the optical fiber after treatment of an affected area and then cutting the optical fiber exposed to the outside upon treatment of the affected area using a cutter.

In addition, it is easy to cut the optical fiber with a cutter, and the cutter is detachably connected to the rear side of the main body. Therefore, it is easy to use and store the cutter.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Hereinafter, the configuration and operation of preferred embodiments of the present invention will be described in detail with reference to the accompanying drawings. Here, in the case of assigning the reference numerals to the components of the drawings, it should be noted that, with respect to the same components, the same reference numerals are used even in different drawings.

The present invention provides a handpiece laser treatment apparatus for treating an affected area by radiating lasers thereto. The present treatment apparatus can adjust the drawn length of optical fiber in which laser is irradiated and it can be re-used conveniently and hygienically by cutting a part of the optical fiber exposed to the outside upon treatment of an affected area and then drawing out the non-exposed optical fiber.

Below, the present invention will be described in detail with reference to the accompanying drawings.

Figure 2:
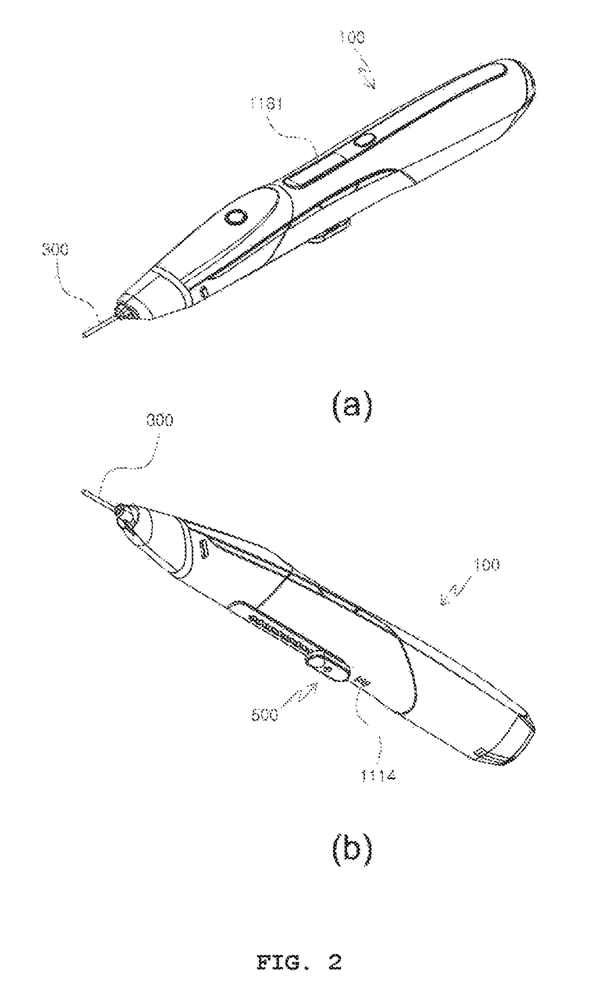
FIG. 2 is a perspective view of the handpiece laser treatment apparatus capable of adjusting the length of an optical fiber according to one embodiment of the present invention.
Figure 3:
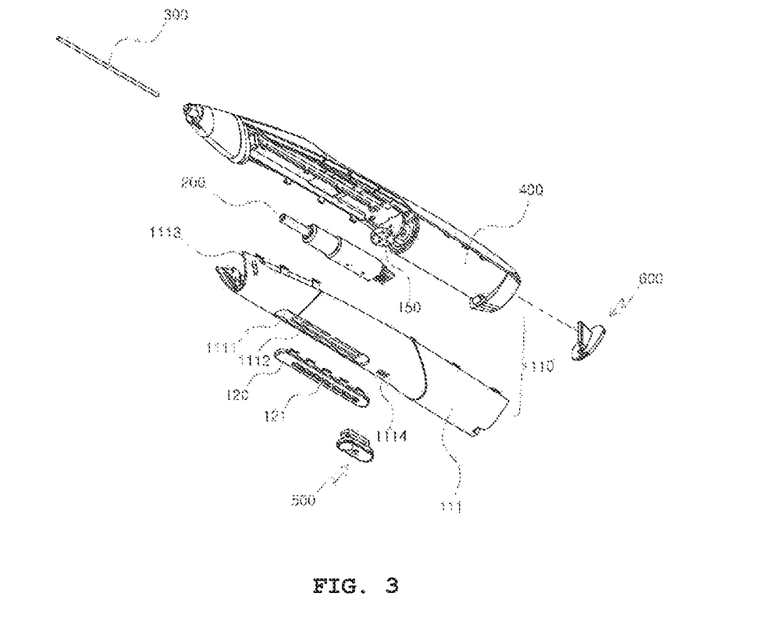
FIG. 3 is an one-way exploded perspective view of the handpiece laser treatment apparatus capable of adjusting the length of an optical fiber according to one embodiment of the present invention.
Figure 4:
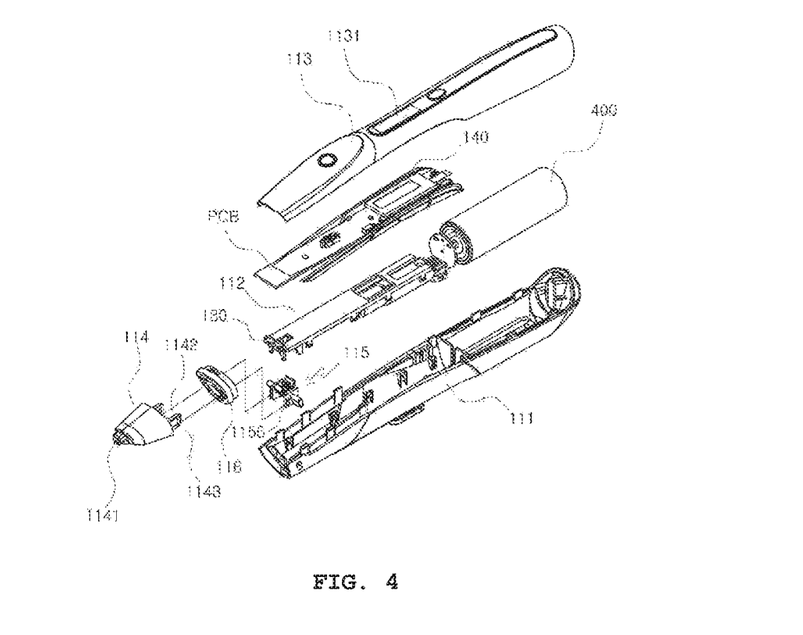
FIG. 4 is another way exploded perspective view of the handpiece laser treatment apparatus capable of adjusting the length of an optical fiber according to one embodiment of the present invention.
Figure 5:
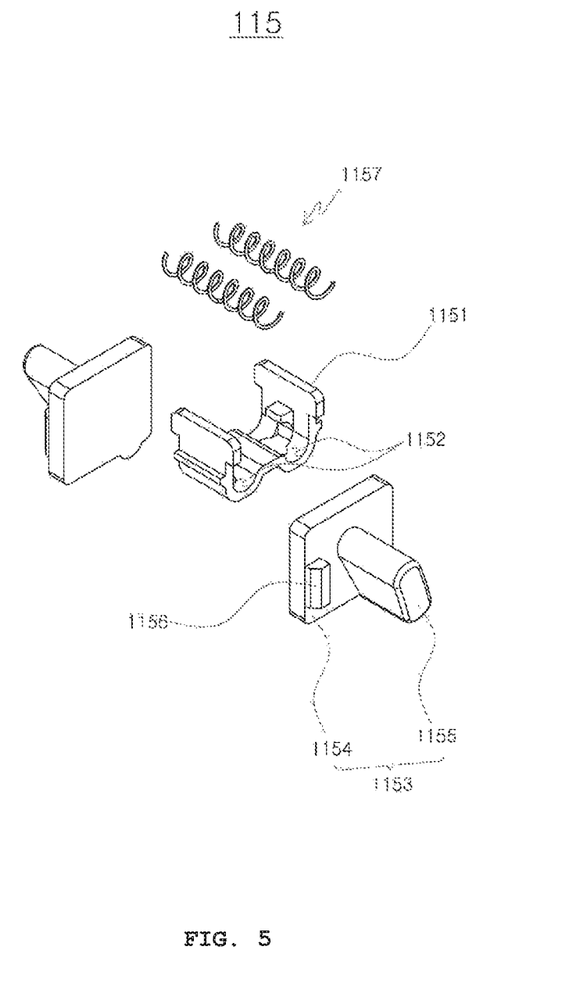
FIG. 5 is an exploded perspective view of a cover detaching mechanism according to one embodiment of the present invention.
Figure 6:
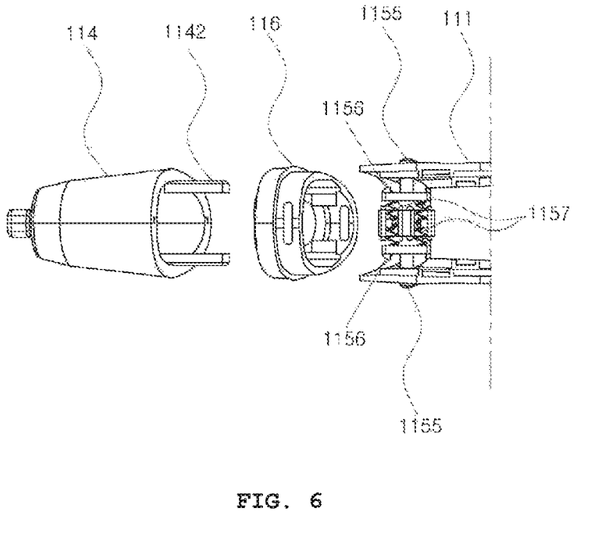
FIG. 6 is an exploded perspective view of the handpiece laser treatment apparatus capable of adjusting the length of an optical fiber according to one embodiment of the present invention.
Figure 7:
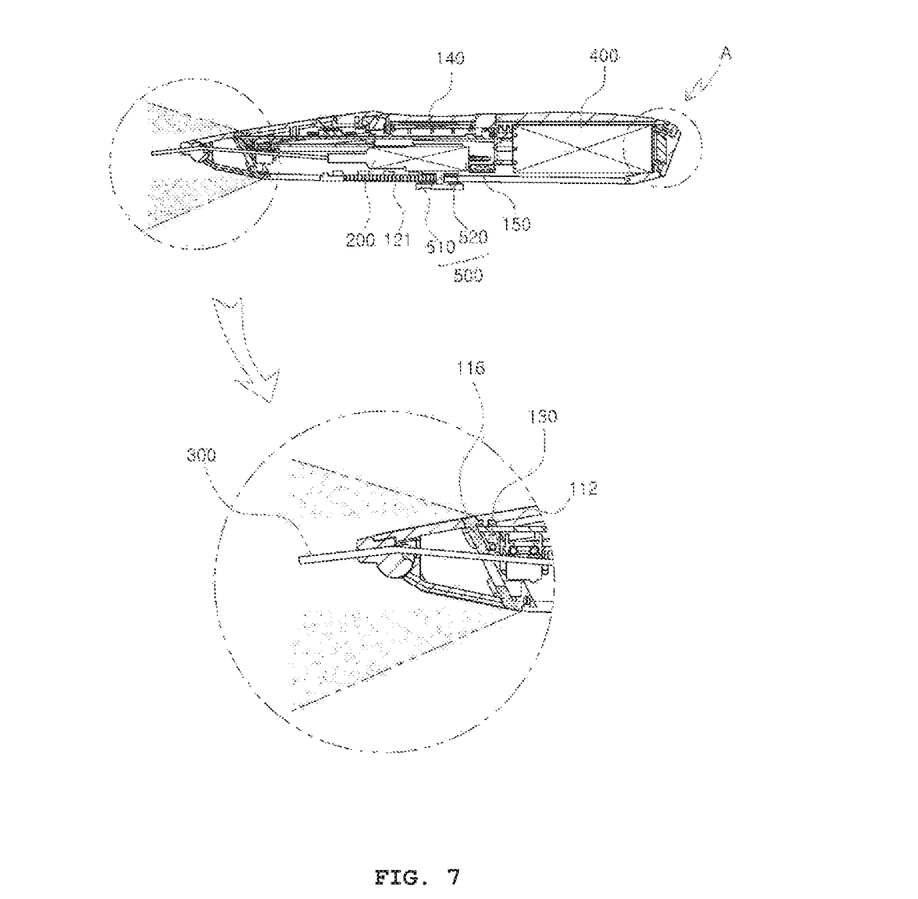
FIG. 7 is is a cross-sectional view of the handpiece laser treatment apparatus capable of adjusting the length of an optical fiber according to one embodiment of the present invention.
Figure 8:
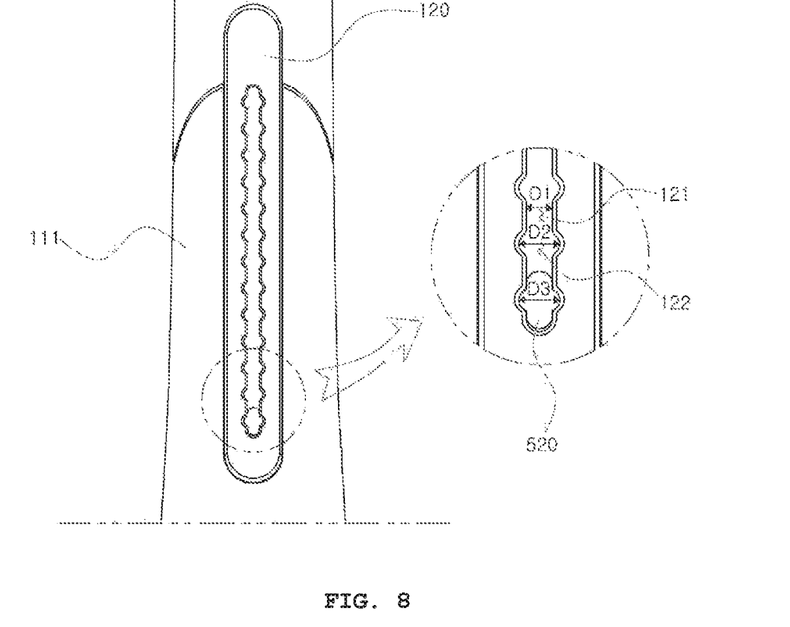
FIG. 8 is a bottom view of the handpiece laser treatment apparatus capable of adjusting the length of an optical fiber according to one embodiment of the present invention.

FIG. 2(a) is a perspective view as seen from the front upper part of the handpiece laser treatment apparatus capable of adjusting the length of an optical fiber. FIG. 2(b) is a perspective view as seen from the front lower part of the handpiece laser treatment apparatus capable of adjusting the length of an optical fiber. FIG. 3 is an exploded perspective view as seen from the front lower part in order to investigate the basic configuration of the handpiece laser treatment apparatus capable of adjusting the length of an optical fiber. FIG. 4 is an exploded perspective view as seen from the front upper part in order to investigate a detailed configuration of the handpiece laser treatment apparatus capable of adjusting the length of an optical fiber. FIG. 5 is an exploded perspective view of a cover detaching mechanism shown in FIG. 4. FIG. 6 is an exploded perspective view illustrating a head cover, a light projecting unit, a cover detaching mechanism and a part of lower casing in order to investigate how to couple and separate the head cover. FIG. 7 is is a cross-sectional view showing the internal structure of the handpiece laser treatment apparatus capable of adjusting the length of an optical fiber. FIG. 8 shows a partially enlarged view of a bottom side of the handpiece laser treatment apparatus capable of adjusting the length of an optical fiber.

Figure 9:
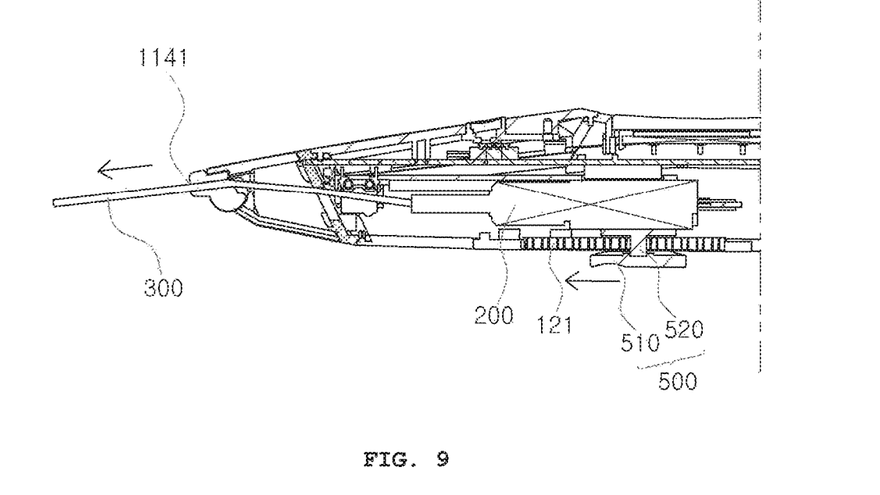
FIG. 9 is an operation state diagram of the handpiece laser treatment apparatus capable of adjusting the length of an optical fiber according to one embodiment of the present invention.
Figure 10:
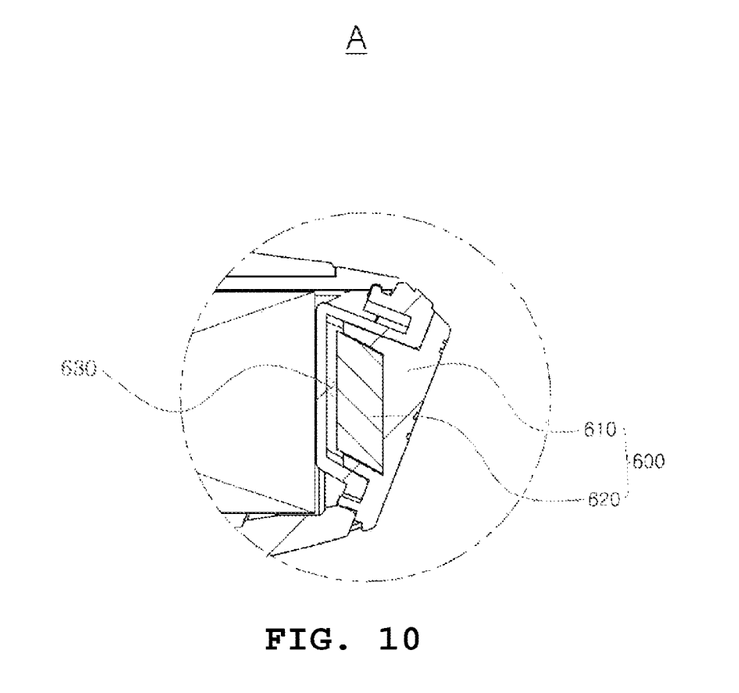
FIG. 10 is a view showing an enlarged portion A of FIG. 7.

FIG. 9 shows an optical fiber in which the slider is moved forwardly and further projected forwardly in the cross-sectional view of FIG. 7. FIG. 10 is an enlarged view of the cutter coupled to the main body.

The handpiece laser treatment apparatus capable of adjusting the length of an optical fiber according to one embodiment of the present application includes a-main body 100, a laser module 200, an optical fiber 300, a power supply unit 400, a slider 500 and a cutter 600 as shown in FIGS. 2 through 10.

The main body (100) is configured such that the laser module 200 is inserted and disposed in the inside and the optical fiber 300 is projected in front of the body as shown in FIG. 2. And the cutter 600 is connected to the rear side of the main body 100. In particular, the main body 100 comprises a casing 110, a slide cover 120, an illumination unit 130, a display unit 140, a speaker 150 and a control unit (not shown).

The casing 110 is configured such that the laser module 200 is inserted and disposed into the inside and the optical fiber 300 is projected to the front side as shown in FIG. 3. Such casing 110 includes a lower casing 111, an inner cover 112, an upper casing 113, a head cover 114, a cover detaching mechanism 115 and a light projecting section 116.

The laser module 200 is inserted inside the lower casing 111, and a movable space in a forward and backward direction is formed. The lower casing 111 has a cover coupling part 1111 for coupling a slide cover 120. In the cover coupling part 1111, a through hole 1112 penetrating upward and downward is formed so as to communicate with a guide groove 121 which is formed in a slide cover 120. Further, a push hole 1113 is formed on both sides in front of the lower casing 111.

Specific description of the push hole 1113 will be given later together with the cover detaching device 115. Further, the lower casing has an outlet part 1114 which sends out an alarm or warning sound generated through a speaker 150.

The inner cover 112 is coupled to the upper pan of the lower casing 111 and an inner space of the casing 110 is divided into top and bottom. The laser module 200 is disposed in the lower space divided by the inner cover 112. The inner cover 112 is mounted with a cover detaching device 115, an illumination unit 130 and the like. Further, the inner cover 112 is mounted with a main PCS which is connected to a display part 140, a speaker 150, and various buttons. Additionally, the main PCS is mounted with a control unit (not shown).

The upper casing 113 is coupled to the upper portion of the lower casing 111 and covers the inner cover 112. As shown in FIG. 4, the upper casing 113 has a display window 1131 for displaying an operation state of the handpiece laser treatment apparatus to the outside. Further, the upper casing 113 has a number of buttons connected with a control unit in order to operate or control the handpiece laser treatment apparatus. In order to operate or control various functions of the handpiece laser treatment apparatus, a number of buttons are also formed between the lower casing 111 and the upper casing 113.

As shown in FIG. 4, the head cover 114 is disposed in front of the lower casing 111 and the upper casing 113 coupled with each other, and a drawn ball 1141 is formed such that the optical fiber 300 is protruded to the outside. In particular, the protrusion 1142 is protruded and formed to the rear side of the head cover 114, and a locking groove 1143 is formed in the protrusion 1142. The protrusion 1142 and the locking groove 1143 have a structure to detachably couple to the lower casing 111. A more detailed description of these detachable structures will be given later.

Meanwhile, the handpiece laser treatment apparatus according to an embodiment of the present invention may comprise a sensor that is capable of detecting the presence or absence of a head cover 114 in order to control the generation of laser depending on the presence or absence of coupling of the head cover 114 and lower casing 111.

The cover detaching mechanism 115 is mounted in front of the inner cover 112 and has the head cover 114 coupled in front of the lower casing 111. In particular, the cover detaching device 115 includes a spring housing 1151, a push member 1153 and a push spring 1157 as shown in FIG. 5.

The spring housing 1151 is mounted on a front lower portion of the inner cover 112, both ends being formed to bend to the upper portion. And the spring housing 1151 has spring groove 1152 in which a push spring 1157 is disposed.

The push member 1153 is disposed on both sides of the spring housing 1151. The push member 1153 includes a support plate 1154 which is disposed on both sides of the spring housing 1151, and a push button 1155 which is formed to project from the push hole 1113 and inserted into a support plate 1154. Further, the support plate 1154 has a locking protrusion 1156 which is attached in front of the lower casing 111. Thus, if the protrusion 1142 is inserted in the inner portion of the lower casing 111, coupling of the lower casing 111 and the head cover 114 is maintained while the locking protrusion 1156 is inserted in the locking groove 1143.

The push spring 1157 is inserted into the spring groove 1152 and disposed between two push members 1153. Further, the push spring 1157 is configured such that both ends are in contact with the support plate 1154 to support the push member 1153 on both sides, thereby the push-button 1155 is protruded to the outside through a push hole 1113.

Thus, in a state in which the locking protrusion 1156 is inserted into the locking groove 1143, the coupled state of the head cover 114 and the lower case 111 is maintained while the locking protrusion 1156 is not arbitrarily detached from the locking groove 1143. If the push button 1155 is pressed in the direction of the push spring 1157, the push spring 1157 is compressed and the locking protrusion 1156 inserted into the locking groove 1143 is detached from the locking groove 1143, thereby separating the head cover 114 from the lower casing 111. Thereafter, when an external force pressing the push-button 1155 is removed, the push button 1155 is protruded to the outside of the lower casing 111 through a push hole 1113 by the elastic force of the push spring 1157 as shown in FIG. 6.

The light projecting section 116 is made of a light-transmitting material and disposed between the lower casing 111, and the upper casing 113 and the head cover 114 which are coupled with each other. In the light projecting section 116, light generated from the illumination unit 130 is transmitted to irradiate to the outside as shown in FIG. 7. In particular, the light projecting section 116 is produced by the light diffusing acrylic material, and the light irradiated through the light projecting section 116 to the outside lights an affected area upon its treatment. Moreover, the light projecting section 116 improves the aesthetics of the handpiece laser treatment apparatus appearance as a design element.

The slide cover 120 is attached to the casing 110. In particular, the slide cover 120 is coupled to the cover coupling section 1111 of the lower casing 111 and, as shown in FIG. 8, a long guide groove 121 is formed in the forward and backward direction (in the vertical direction in Figure).

The guide groove 121 communicates with the through hole 1112. More particularly, the slide cover 120 is made of an elastic material such as a rubber. Further, in the slide cover 120, a plurality of fixing grooves 122 communicating with the guide groove 121 are formed apart from each other in the forward and backward direction. In this case, the width (D1) of the guide groove 121 is smaller than the width (D2) of the fixing groove. In these guide grooves 121, the slider 500 is inserted, and the laser module 200 and the slider 500 are connected. Further, for the slider 500, its movement is limited by the guide groove 121. That is, the slider 500 is inserted into any one fixing groove 122 of a large number of the fixing grooves 122, and thus the movement is limited. When an external force is applied to the slider 500 by a user, the slide cover 120 is elastically deformed while the slider 500 moves along the guide groove 121, thereby extending the guide groove 121.

The illumination unit 130 is a LED module, and is attached hi front of the inner cover 112 as shown in FIG. 4. Moreover, as shown in FIG. 7, the light generated from the illumination unit 130 is irradiated to the outside through the light projecting section 116. As described above, the light generated from the illumination unit 130 and irradiated to the outside through the light projecting section 116 shines the affected area upon treatment of the affected part, facilitating the treatment of the affected area and improving the aesthetics of the handpiece laser treatment apparatus appearance.

The display unit 140 is mounted inside the upper casing 113 and displays an operation state of the handpiece laser treatment apparatus through a display window 1131 which is formed in the upper casing 113.

The speaker 150 is mounted inside the lower casing 111 and send out an alarm or warning sound and the like through the outlet part 1114.

The control unit (not shown) is mounted on the main PCB and connected to a laser module 200, a display unit 140, a speaker 150 and the like. The control unit can control the laser generation or operate a display unit 140, a speaker 150 and the like through the operation of various buttons by the user or depending on the operation state of the handpiece laser treatment apparatus. As described above, when providing the sensor for detecting the presence or absence of coupling of the head cover 114, the control unit controls the laser module 200 based on the signal of the sensor and cut off the generation of laser.

The laser module 200 generates a laser and is inserted and disposed inside the lower casing 111 so as to be moved in the forward and backward direction as shown in FIG. 9.

The optical fiber 300 is connected to the laser module 200 and transmits the laser generated by the laser module 200 to the outside so that the laser is irradiated to the affected area. This optical fiber 300 can adjust the length which is projected in front of the head cover 114 through the drawing ball 1141 and projected in front of the head cover 114 by the operation of the slider 500.

The power supply unit 400 is inserted to the rear side of the casing 110 and supplies an electric power to the main PCB, laser module 200 and the like.

The slider 500, as shown in FIG. 9, moves the laser module 200 in the forward and backward direction of the main body 100 and adjusts the length of the optical fiber 300 which is projected in front of the main body 100. The slider 500 includes a moving part 510 and a connecting part 520. The moving part 510 moves in the forward and backward direction of the casing 110 along the guide groove 121 by the user. The connecting part 520 is inserted into the guide groove 121 and connected to the laser module 200 and the moving part 510. In particular, as shown in FIG. 8, the width (D3) of the cross-section of the moving part 510 is larger than the width (D1) of the guide groove 121 and equal to the width (D2) of the fixing groove 122.

Further, unlike specific embodiments as as shown in Figure, the width (D3) of the cross section of the moving part 510 may be formed to be smaller than the width (D2) of the fixing groove 122. Thus, in a state where the connecting part 520 is inserted and disposed in the fixing groove 122, the slider 500 does not arbitrarily move along the guide groove 121. If the external force is applied to the moving part 510, the connecting part 520 moves along the guide groove 121, and the slide cover 120 is elastically deformed by the connecting part 520, thereby extending the guide groove 121. Thus, if the user allows to move the moving part 510, the laser module 200 connected to the moving part 510 via a connecting part 520 as shown in FIG. 9 is moved together, thereby adjusting the drawn length of the optical fiber 300 which is connected with the laser module 200.

The cutter 600 is used for cutting the optical fiber 300 and it is detachably coupled to the rear side of the body 100, as shown in FIG. 10. In particular, the cutter 600 includes a coupling body 610 which is detachably coupled to the rear side of the casing 110; and a cutting blade 620 which is mounted to the coupling body 610. In order to detachably couple the cutter 600 to the rear side of the casing 110, a blade groove 630 in which the cutting blade is inserted is formed to the rear side of the casing 110. The cutter 600 is used for cutting the optical fiber 300 which is exposed to the outside upon treatment of the affected part after treating the affected part using the handpiece laser treatment apparatus. The cutter 600 is detachably provided to the rear side of the main body 100. Therefore, it is easy to use and store the cutter 600.

The handpiece laser treatment apparatus as described above can draw out the optical fiber using the slider 500, thereby adjusting the length of the optical fiber 300 which is protruded in front of the body 100. After treating the affected area and drawing out the optical fiber 300, the optical fiber 300 exposed to the outside upon treatment of the affected area is cut by using the cutter 600, thereby the optical fiber 300 can be conveniently and hygienically re-used.

The handpiece laser treatment apparatus capable of adjusting the length of the optical fiber according to the present invention is not limited to the embodiments described above and various modifications and changes can be made to the invention within the range in which the technical idea of the present invention is allowed.

What is claimed is:

1. A laser treatment apparatus including a handpiece capable of adjusting a projected length of an optical fiber, comprising:
   a laser module for generating a laser beam;
   a main body in which the laser module is inserted and disposed;
   an optical fiber that is connected to the laser module so that the laser beam is irradiated to an outside of the laser module, the optical fiber being projected from a distal end of the main body toward a target treatment site;
   a slider for adjusting a length of the optical fiber projected from the main body; and
   a cutter for cutting the optical fiber,
   wherein the cutter comprises a coupling body which is detachably coupled to a rear side of the main body, and a cutting blade which is attached to the coupling body, wherein a blade groove in which the cutting blade is inserted is formed at the rear side of the main body.

2. The laser treatment apparatus including a handpiece capable of adjusting a projected length of an optical fiber according to claim 1 wherein
   the main body comprises a guide groove; and
   the slider comprises a moving part to move along the guide groove back and forth in a longitudinal direction of the main body, and a connecting part which is inserted into the guide groove and connects the laser module and the moving part.

3. The laser treatment apparatus including a handpiece capable of adjusting a projected length of an optical fiber according to claim 2 wherein the main body comprises a plurality of fixing grooves communicating with the guide groove, the plurality of fixing grooves being formed spaced apart from each other in a longitudinal direction of the main body; a width of the guide groove being smaller than a width of the fixing groove; and a width of the cross-section of the connecting part being larger than the width of the guide groove and less than or equal to the width of the fixing groove.

4. The laser treatment apparatus including a handpiece capable of adjusting a projected length of an optical fiber according to claim 2 wherein the main body comprises:
   a casing in which the laser module is inserted and disposed; and
   a slide cover which is mounted on the casing and comprises the guide groove, wherein the slide cover is made of an elastic material and is elastically deformed upon movement of the slider, thus extending the width of the guide groove.

* * * * *